United States Patent [19]
Lambert

[11] Patent Number: 5,398,673
[45] Date of Patent: Mar. 21, 1995

[54] RESUSCITATOR-SNORKEL FOR LAND OR WATER USE

[75] Inventor: Barnum B. Lambert, San Jose, Calif.

[73] Assignee: Environmental Support Systems, Inc., San Jose, Calif.

[21] Appl. No.: 165,100

[22] Filed: Dec. 10, 1993

[51] Int. Cl.$^6$ ............................................ A61M 16/00
[52] U.S. Cl. ........................ 128/202.28; 128/202.29; 128/203.11; 128/205.24; 128/201.11; 128/201.28
[58] Field of Search .................. 128/202.28, 202.29, 128/203.11, 205.13, 205.24, 201.11, 201.28

[56] References Cited

U.S. PATENT DOCUMENTS

| | | | |
|---|---|---|---|
| 3,046,978 | 7/1962 | Lea | 128/205.13 |
| 3,099,985 | 8/1963 | Wilson et al. | 128/203.11 |
| 3,262,446 | 7/1966 | Stoner | 128/205.13 |
| 3,948,255 | 4/1976 | Davidson | 128/202.28 |
| 4,360,017 | 11/1982 | Barlett | 128/202.28 |
| 4,449,525 | 5/1984 | White et al. | 128/203.11 |
| 4,579,114 | 4/1986 | Gray et al. | 128/203.11 |
| 4,834,085 | 5/1989 | Webster, II | 128/203.11 |
| 4,856,506 | 8/1989 | Jinotti | 128/203.11 |
| 4,881,540 | 11/1989 | Vigilia | 128/202.28 |
| 4,886,057 | 12/1989 | Nave | 128/203.11 |
| 4,909,245 | 3/1990 | Wollenhaupt | 128/203.11 |
| 4,942,873 | 7/1990 | Irwin et al. | 128/203.11 |
| 4,998,530 | 3/1991 | DonMichael | 128/203.11 |
| 5,005,568 | 4/1991 | Loescher et al. | 128/202.28 |
| 5,020,530 | 6/1991 | Miller | 128/203.28 |
| 5,095,898 | 3/1992 | Don Michael | 128/203.11 |
| 5,119,809 | 6/1992 | Gerson | 128/203.11 |
| 5,152,283 | 10/1992 | Yamasaki | 128/202.28 |
| 5,230,330 | 7/1993 | Price | 128/203.11 |

OTHER PUBLICATIONS

Photocopy of specification sheet for a breathing assist device made in Europe and sold under the trademark Lifeway.

*Primary Examiner*—Edgar S. Burr
*Assistant Examiner*—Aaron J. Lewis
*Attorney, Agent, or Firm*—Virginia H. Meyer

[57] ABSTRACT

The present invention is an assisted breathing device which allows a rescuer or emergency care giver to administer mouth-to-mouth type resuscitation to a victim or patient on land or in the water, without the rescuer or emergency care giver having to come in direct contact with the victim or patient's lips, exhaled air or body fluids. The assisted breathing interface device comprises, in combination, a tubular conduit or housing, a slide valve, and a spring or tension loaded valve member on the slide valve. The tubular housing has two open end orifices, at least one defined side wall opening and a central air passageway for the flow of air from a first person (rescuer or emergency aid giver) to a second person (victim or patient) during inflation or inhalation, and from the second person to defined side wall opening(s), and then the atmosphere, during exhalation; a slide valve, with at least one air passageway therein; and a valve member positioned at the air passageway in the slide valve, to control the flow of air through the air passageway on the slide valve. In operation the flow of air through the central passageway in the assisted breathing device is controlled by the slide valve and its valve member positioned at the air passageway in the slide valve, which operates to either open the passageway in the slide valve or close it, so that air can be directed through the central passageway in the device and the passageway in the slide valve from the first person to the second person as needed, but exhaled air from the second person does not return through the passageway in the slide valve to the first person.

20 Claims, 6 Drawing Sheets

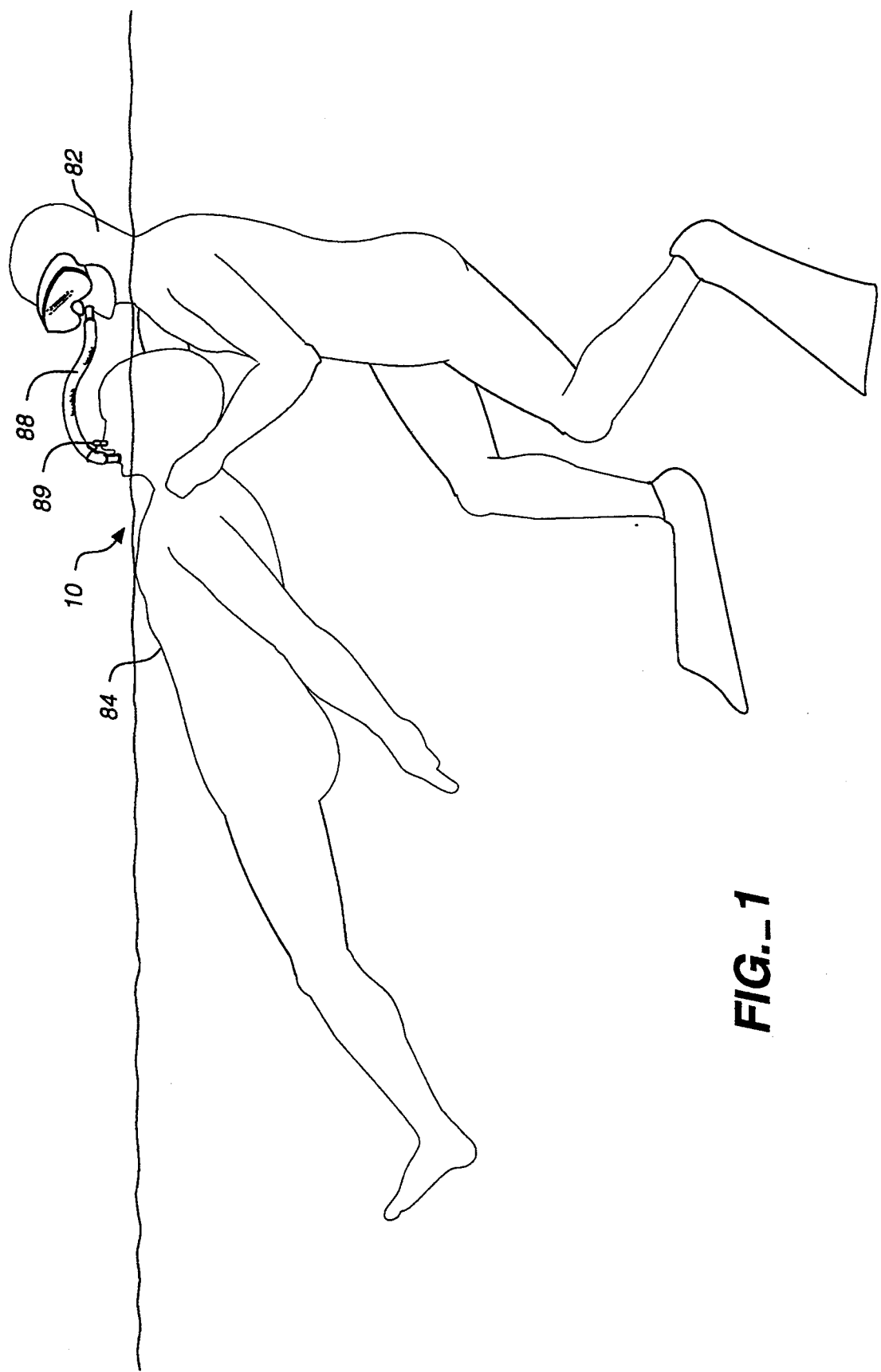
FIG._1

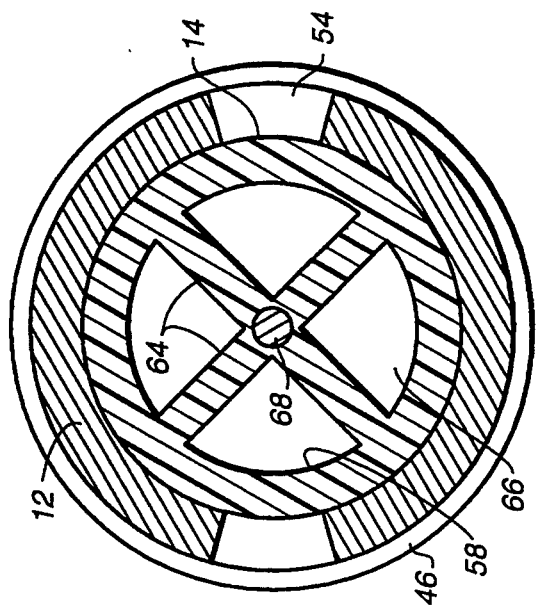
FIG._5
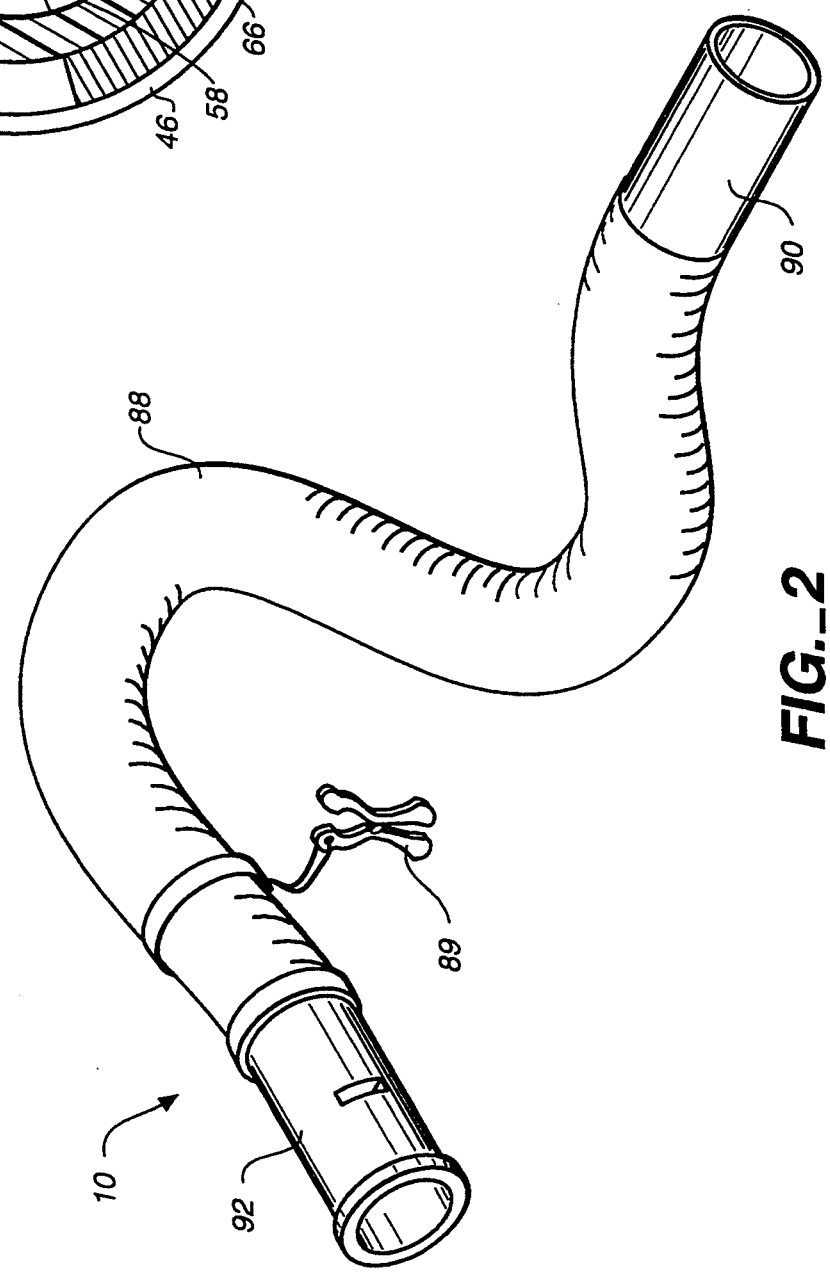
FIG._2

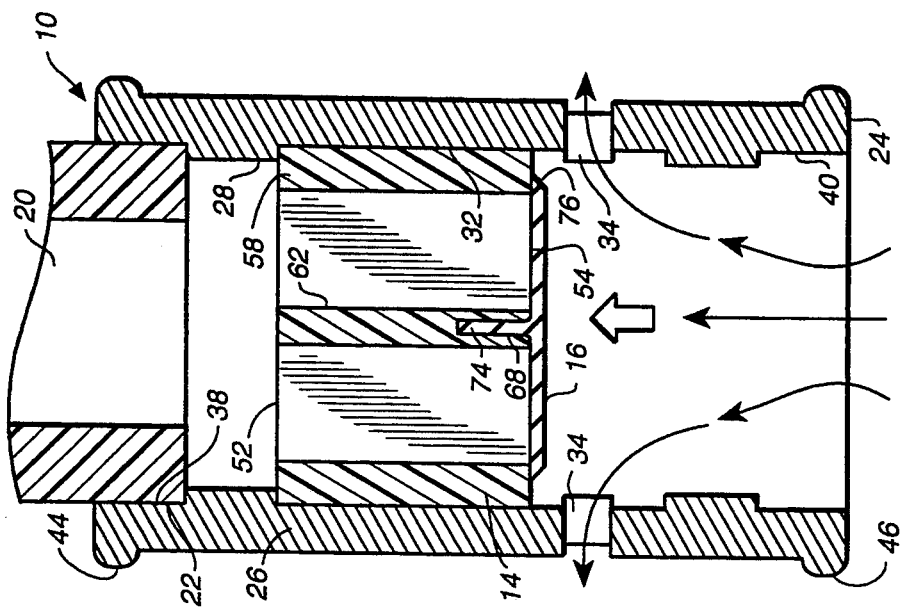
FIG._4
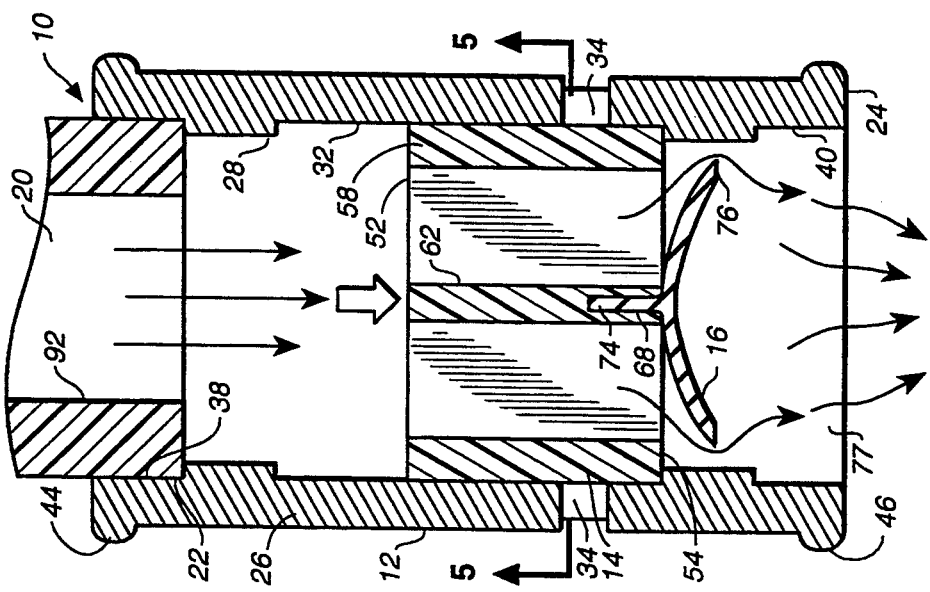
FIG._3

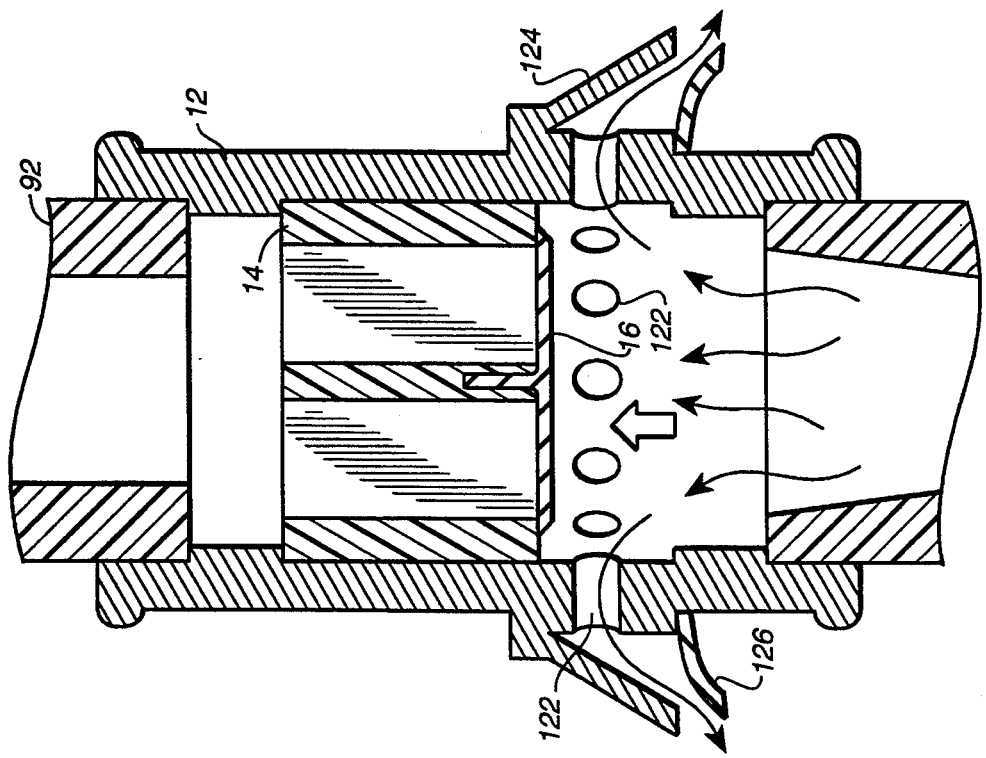
FIG._6
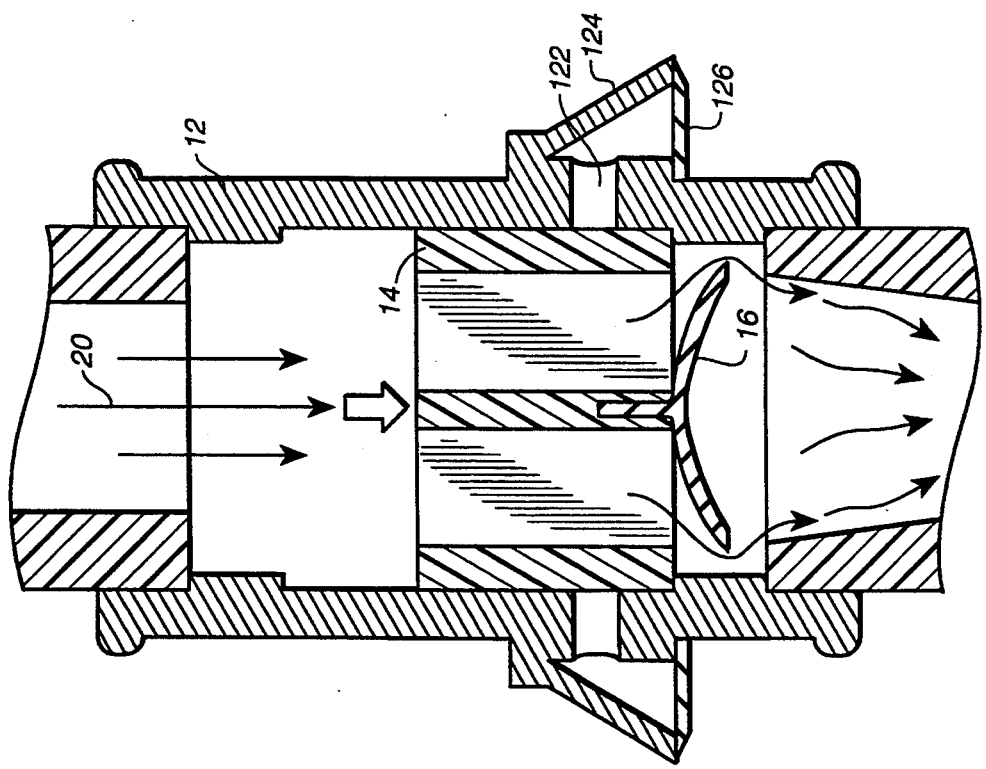
FIG._7

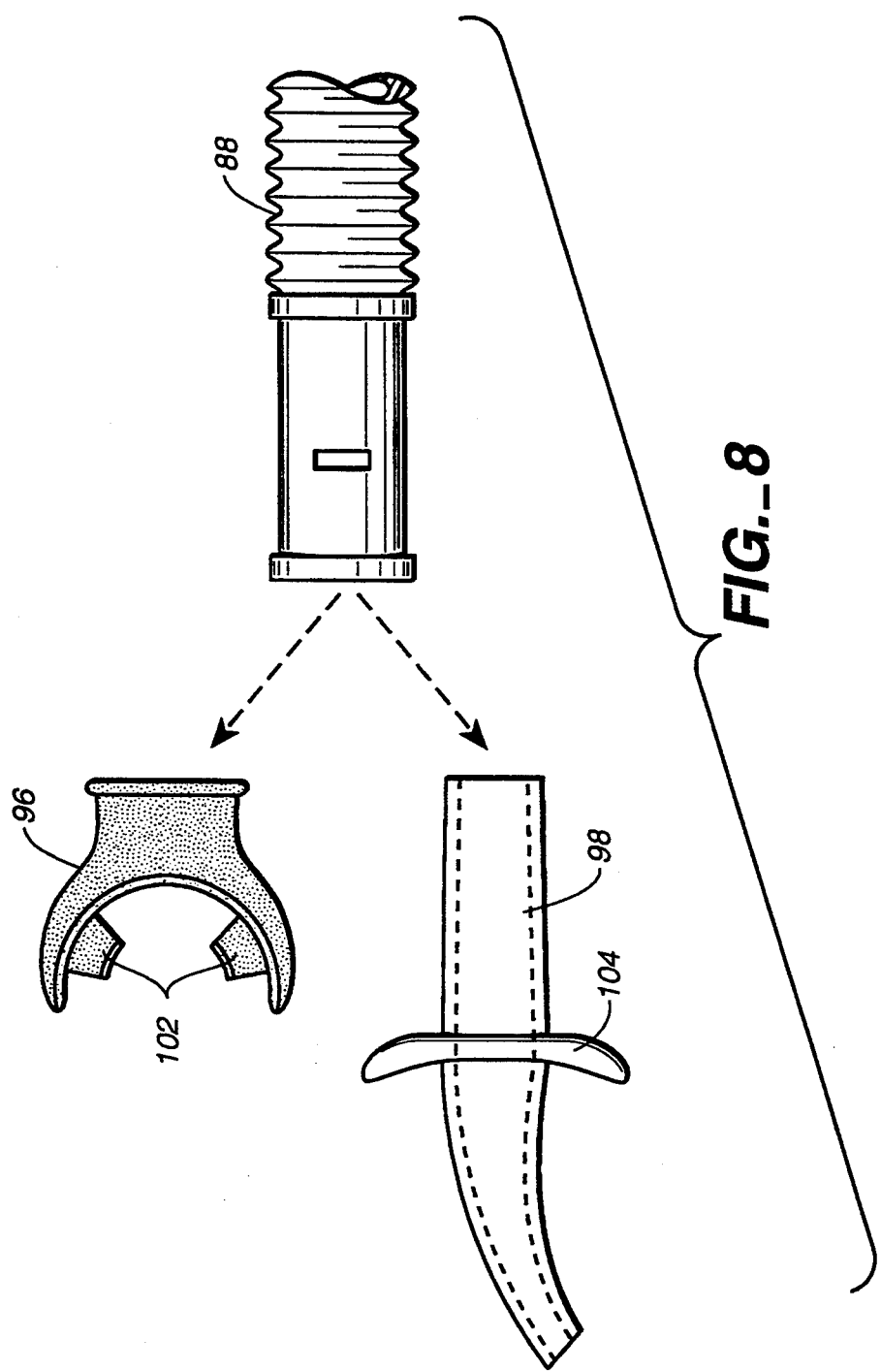
FIG._8

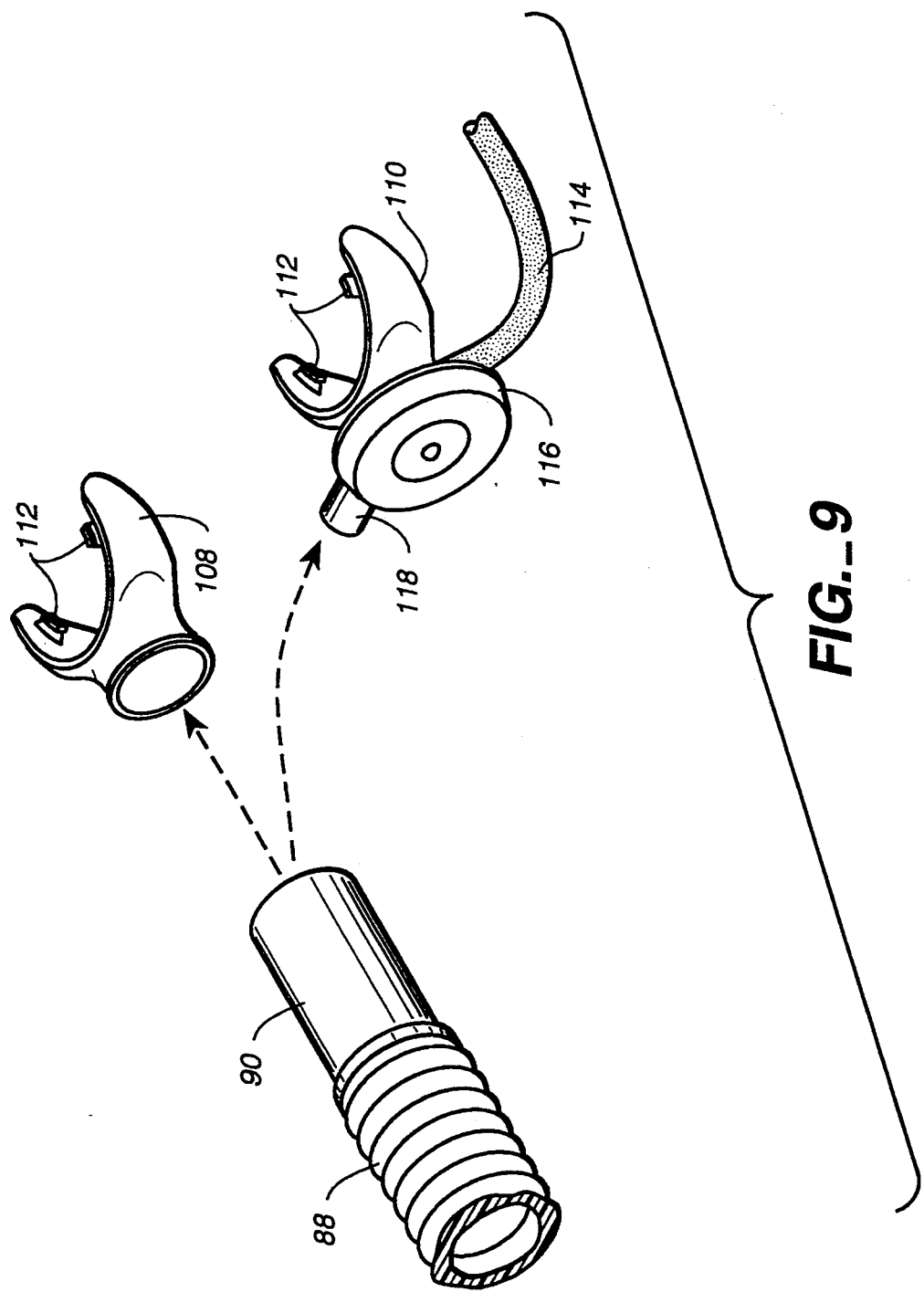
FIG._9

RESUSCITATOR-SNORKEL FOR LAND OR WATER USE

FIELD OF THE INVENTION

This invention relates to assisted breathing interface devices, particularly assisted breathing interface devices which allow a rescuer or emergency care giver to administer mouth-to-mouth type resuscitation to a victim or patient on land or in the water, without the rescuer or emergency care giver having to come in direct contact with the victim or patient's lips, exhaled air or body fluids.

BACKGROUND OF THE INVENTION

If a victim or patient has stopped breathing, unless air is promptly and at regular intervals forced into the lungs of that individual, the victim or patient will die. If mechanical resuscitation equipment is not available, rescuers and emergency care providers are forced to rely on mouth-to-mouth resuscitation when attempting to keep the person who has stopped breathing from dying. With mouth-to-mouth resuscitation, air is forced, at regular intervals, from the lungs of the rescuer or emergency care giver into the lungs of the victim or patient who has stopped breathing.

Classic mouth-to-mouth resuscitation requires direct contact between the mouth of the rescuer and the mouth of the victim. Consequently, rescuers using classic mouth-to-mouth techniques are at risk of catching communicable diseases from the victim. In addition, victims may have blood or other body fluids in their mouths or on their lips. This leads to even greater risk of contracting blood and fluid born diseases such as AIDS and hepatitis if mouth-to-mouth resuscitation is administered using classic techniques. This risk to emergency care workers and others who are called upon to administer mouth-to-mouth resuscitation led to a U.S. Federal Occupational Safety and Health Administration (OSHA) regulation regarding occupational exposure to blood borne pathogens such as those which cause AIDS and hepatitis. The regulation, which went into effect on Jun. 4, 1992, requires all employers to protect employees from occupational exposure to the AIDS virus (HIV) and other blood borne disease-causing agents. With this regulation in force, the teaching of classic mouth-to-mouth resuscitation techniques which require direct skin, fitlid or gas contact is prohibited. Instead, employees must be taught to use protective interface devices when administering mouth-to-mouth resuscitation so that direct skin contact, and fitlid or gas exchange between the rescuer and victim is eliminated.

A number of protective interface devices are available which have been designed to protect rescuers and emergency care workers called upon to administer mouth-to-mouth type resuscitation to a victim or patient who is "on land". These devices include: the Assisted Breathing Interface Device disclosed in U.S. Pat. No. 4,886,057 issued Dec. 12, 1989 to Nave; the Compact Disposable Mouth-To-Mouth Resuscitation Device disclosed in U.S. Pat. No. 4,909,245 issued Mar. 20, 1990 to Wollenkaupt; the Isolation Valve disclosed in U.S. Pat. No. 5,005,568 issued Apr. 9, 1991 to Loescher et al.; the Resuscitation Aids disclosed in U.S. Pat. Nos. 4,998,530 and 5,095,898 issued Mar. 12, 1991 and Mar. 17, 1992, respectively, to Michael; and the Mouth-To-Mouth With Valve And Barrier device disclosed in U.S. Pat. No. 5,119,809 issued Jun. 9, 1992 to Gerson.

Unfortunately, none of these interface devices are really suitable for use if the victim is in the water, when it is often necessary to provide aid from either side, or from behind the victim. These prior devices are also not suitable for use as a snorkel if the water or land victim is capable of breathing on his or her own, but needs a "snorkel" to reach a source of fresh air. In addition, presently available interface devices are also not entirely suitable for use with victims who can breath on their own, since presently available devices do not indicate to the aid giver that a victim is breathing. Thus there is a need for an assisted breathing interface device which not only assures that the rescuer or aid giver will not come in contact with the victim's lips, exhaled air or body fluids, but can be used "on land" or "in the water", to provide mouth to mouth type resuscitation to a victim who is in the water. In addition, there is a need for an assisted breathing interface device that can also function as a "snorkel", and for an assisted breathing device that, when used with a victim who can breath on his or her own, will indicate to the aid giver that the victim is breathing. The present invention has been developed to address these and related needs.

SUMMARY OF THE INVENTION

The present invention discloses a novel assisted breathing device which allows a rescuer or emergency care giver to administer mouth-to-mouth type resuscitation to a victim or patient on land or in the water, without the rescuer or emergency care giver having to come in direct contact with the victim or patient's lips, exhaled air or body fluids. The assisted breathing interface device comprises, in combination, a tubular conduit or housing, a slide valve, and a spring or tension loaded valve member on the slide valve. The tubular housing has two open end orifices, at least one defined side wall opening and a central air passageway for the flow of air from a first person (rescuer or emergency aid giver) to a second person (victim or patient) during inflation or inhalation, and from the second person to defined side wall opening(s), and then the atmosphere, during exhalation; a slide valve, with at least one axial air passageway therein; and a spring or tension loaded valve member positioned at the axial air passageway in the slide valve, to control the flow of air through the air passageway(s) on the slide valve.

In operation the flow of air through the central passageway in the assisted breathing device is controlled by the slide valve and its spring or tension loaded valve member, which operates to either open the axial air passageway in the slide valve or close it, so that air can be directed through the central passageway in the device and the axial air passageway in the slide valve from the first person to the second person as needed, but exhaled air from the second person does not return through the axial air passageway in the slide valve, and back to the first person.

As indicated above, the slide valve contains a tension or spring loaded valve member, for example a popper valve or a flapper valve, which functions to open the axial air passageway from the first person to the second person after the slide valve has moved to close the defined side wall opening(s) by which exhaled air from the second person is exhausted to the atmosphere. When the tension or spring loaded valve is a flapper valve, it opens by deformation from its normally planar state by the differential pressure across its surface.

When the valve is a poppet valve, it opens as the result of controlled movement out or away from the port or axial air passageway in the slide valve where it is seated, by the force of the air coming through the passageway.

In an alternate embodiment that is particularly useful when the victim is in the water, a conical cover and an elastomeric washer or ring valve member are provided to prevent water from entering the defined opening(s) in the side wall by which exhaled air from the second person is delivered to the atmosphere.

The device of the invention may also include adapters coupled to the housing. Such adapters include flexible or inflexible tubes or hoses, and mouth pieces.

The assisted breathing device of the present invention is suitable for use on land, or in the water, and it is necessary to provide aid from either side, or from behind the victim. It is also suitable for use as a snorkel if the water or land victim is capable of breathing on his or her own, but needs a snorkel to reach a source of fresh air. In addition, the assisted breathing device of the invention is especially suitable for use with victims who can breath on their own since the movement of the slide valve is an indication to the aid giver that the victim is breathing.

These and other features, aspects, and advantages of the present invention will become better understood with regard to the following description, appended claims, and accompanied drawings.

DRAWINGS

FIG. 1 is a perspective view of a rescuer utilizing an assisted breathing device of the present invention to give artificial mouth-to-mouth respiration to a victim, when both the emergency care administrator and the victim are in the water.

FIG. 2 is a perspective view of an assisted breathing device of the present invention.

FIG. 3 is side sectional view of the victim or patient end of one embodiment of the present invention in the inflate or inhale mode, with the slide valve in a second orientation.

FIG. 4 is side sectional view of the victim or patient end of one embodiment of the present invention in the or exhale mode, with the slide valve in a first orientation.

FIG. 5 is a cross-sectional view of the victim or patient end of the present invention taken substantially about lines 5—5 of FIG. 3.

FIG. 6 is side sectional view of the victim or patient end of another embodiment of the present invention in the inflate or inhale mode.

FIG. 7 is side sectional view of the victim or patient end of another embodiment of the present invention in the exhale mode.

FIG. 8 is a perspective view of adapters that can be affixed to the victim or patient end of the present invention.

FIG. 9 is a perspective view of adapters that can be affixed to the aid giver or rescuer's end of the present invention.

DETAILED DESCRIPTION OF THE INVENTION

Referring now to the drawings in detail, and in particular to FIG. 1 thereof, preferred embodiments of assisted breathing interface devices embodying the principles and concepts of the present invention and generally designated by the reference numeral 10 will be described.

Specifically, it will be noted with reference to FIGS. 1 through 5, 8 and 9 that the present invention is an assisted interface device 10 comprised of conduit or housing 12 (hereinafter housing), sliding valve 14, and tension or spring loaded valve member 16. According to the teaching of the invention, these components are configured and assembled to allow a rescuer or emergency aid giver (the first person) to administer mouth-to-mouth type resuscitation to a victim or patient (the second person) on land or in the water, without the rescuer or emergency aid giver having to come in direct contact with the victim or patient's lips, exhaled air or body fluids.

More specifically, housing 12 is preferably tubular in configuration with a longitudinal central axis 20. Tubular housing 12 has an air-entry end 22 and an air-passage end 24. It also has a generally cylindrical side wall 26 between ends 22, 24. Side wall 26 has an essentially circular cross-sectional configuration on its exterior, which extends along the majority of its axial extent. Side wall 26 also has an axial bore 28 with circular cross-sections of varying diameters internally. A central extent of bore 28 is formed of an increased cross-sectional diameter to constitute slideway 32. Slideway 32 has a predetermined length. It is also formed with at least one radial aperture 34 extending through side wall 26 in slideway 32. Aperture(s) 34 are formed at air passage end 24 of housing 12 proximate to air passage orifice 77. Areas 38 and 40 of increased cross-sectional diameters are formed in the bore at air-entry end 22 and air-passage end 24 for coupling with supplemental components as might be required for a particular application. The exterior of housing 12 may have annular shoulders 44 and 46 for adding rigidity to the housing, and for coupling adapters.

A second component of device 10 is tubular slide valve 14, which is formed with a central longitudinal axis co-incident with the central longitudinal axis 20 of housing 12. Valve 14 has an air-entry end 52 situated towards air-entry end 22 of housing 12 and an air-discharge end 54 situated near air-passage end 24 of housing 12. Valve 14 is formed with a generally cylindrical side wall 58 between its ends 52 and 54. Side wall 58 has an essentially circular cross-sectional configuration along its axial extent externally to slidingly fit within slideway 32. Valve 14 is of an axial length less than the axial length of slideway 32. In this manner when valve 14 is in a first orientation, as shown in FIG. 4, an air path is established from air-passage end 24 of housing 12 through apertures 34. When valve 14 is in a second orientation, as shown in FIG. 3, side wall 58 of valve 14 seals apertures 34 from the passage of air therethrough.

Valve 14 also includes an axial central post 62 attached by radial vanes 64 which extend between the exterior of post 62 and the interior of the cylindrical side wall 58 of valve 14 to define axial passageways 66 through the valve. Post 62 also has a recess 68 in its air-passage end 54.

A tension or spring loaded valve member 16 is a third component of device 10. In preferred form, valve member 16 is a tension loaded flapper valve fabricated of a flexible material with memory, but it may also be a spring loaded poppet valve. Valve member 16 is normally biased into a planar configuration. Valve member 16 has a central projection 74 received for attachment in recess 68 of the post 62, and a radial exterior periphery 76 to normally mate with side wall 58 of slide valve 14 at its air-passage end 54. In this configuration valve member 16 functions to seal of the flow of air through the passageways 66. When valve member 16 is in a planar configuration, air from the patient or victim during exhalation will flow through aperture(s) 34 and not through passageways 66. This is illustrated in FIG. 4. When valve member 16 is a tension loaded flapper valve, it is adapted to assume a second configuration curved away from its center whereby when sliding valve 14 is in the second orientation, air from the air entry end will axially slide valve 14 to close apertures 34 and open passageways 66. This functions to allow the flow of air from the rescuer or aid giver, or the atmosphere when the device is used as a snorkel, to the victim or patient. This is illustrated in FIG. 3. When valve member 16 is a spring loaded popper valve, it is adapted to assume the second configuration when central projection 74 moves a controlled distance within recess 68 of post 62, in the direction of air passage end 24 of housing 12. This movement of central projection 74 causes attached radial exterior periphery 76 to move away from sidewall 58 of slide valve, opening air passages 66. This configuration is not illustrated.

The force required to bend or move valve 16 member to its open, second configuration is greater than that needed to move slide valve 14 from the first orientation position to the second orientation position. In this way, aperture(s) 34 are covered by slide valve 14 before valve 16 member opens to permit the flow of air through axial passageways 66.

Contact between the rescuer and victim, or aid giver and patient may be thus avoided while precluding the transfer of exhaled air and body fluids from the victim or patient to the rescuer or aid giver. In addition, proximity of valve member 16 to the air-passage end 24 of housing 12 creates a minimized "dead space" in areas adjacent thereto. This results ill a reduced rebreathing of exhaled air by the victim or patient, as compared with a device having a greater space of un-exchanged air.

The amount of force needed to move slide valve 14, from the second orientation to the first orientation, when valve member 16 is in sealing configuration, is less than that generated by passive exhalation of the victim or patient. For example, if there is a positive pressure at air entry end 22 relative to air-passage end 24, when valve member 16 is a spring loaded flapper valve, the air resistance of the planar configuration of valve member 16 will result in movement of slide valve 14 to the second orientation, followed by deformation of radially exterior periphery 76 of valve member 16 due to air pressure, when slide valve 14 reaches the end of slideway 32. If valve member 16 is a popper valve, when there is positive pressure at air entry end 22 relative to air-passage end 24, and slide valve 14 has moved to the second orientation, the radial exterior periphery 76 of valve member 16 will move away from side wall 58 of slide valve 14 as the air pressure forces the poppet valve to move in controlled fashion in the direction or air-passage end 22. Conversely, if the air pressure is greater at air-passage end 24, compared to air-entry end 22, then valve member 16 will be planar, and the pressure difference will move slide valve 14 to the first orientation, resulting in air flow out of side aperture 34.

A first adapter is preferably coupled to air-entry end 22 of housing 12 for being coupled to the mouth of rescuer or aid giver 82 for infusing or blowing air into victim or patient 84. A second adapter is preferably coupled to the air-passage end 24 of housing 14 for being coupled to the mouth of victim or patient 84 for receiving air from the rescuer or aid giver 82 and for exhaling air through apertures 34. Note FIGS. 1 and 2. The first adapter is preferably formed of flexible hose 88. The opposite ends 90 and 92 of hose 88 are preferably rigid and of a cylindrical configuration. End 90 may be held in the mouth of the rescuer or emergency aid giver, to administer mouth-to-mouth type resuscitation to a victim or patient. The second end 92 of hose 88 is adapted to be coupled to housing 12 with the output end of housing 12 in the victim or patient's mouth. In the embodiment shown in FIG. 1, this activity is being conducted in the water.

FIG. 8 illustrates devices adapted to couple the mouth of the victim or patient with the output or air-passage end 24 of housing 12. Device 96 is adapted to be coupled with the output end 24 of housing 12, or an end (90, 92) of flexible hose 88, at its first end and adapted to be received into the mouth of the victim or patient at the second end. The second end may be provided with spacers 102 to be positioned between the teeth of the wearer to hold open the mouth to assist in breathing as air is moved through an aperture through device 96. Device 98 is similar in that it has a first end positionable inside the substantially cylindrically-shaped output 40 of the end of housing 24. Its opposite end is elongated and curved for depressing the outer tongue and being positioned part way down the throat of the victim or patient. An enlargement 104 extends on the face of the victim or patient over the lips to preclude the device from sliding excessively into the throat of the victim or patient, and to provide an air tight seal.

Nose clips 89 (see FIG. 1) are useful for closing the nasal passages of the victim or patient, to prevent nasal breathing, and may be tethered to tube 90 or device 98, so they are readily available when needed.

FIG. 9 illustrates two additional devices which may be coupled to tube 90 to assist the rescuer or aid giver in administering aid to the victim or patient. The first of such devices is a mouthpiece 108 similar in construction to device 96. Device 108, however, is adapted to be held securely in the mouth of the rescuer or aid giver, providing an air-tight seal when blowing into tube 88. With this device the rescuer or aid giver inhales through his or her nose. Device 110 is an alternate form of the device with a mouthpiece similar to that of device 108. It also includes projections 112 for being received between the teeth of the rescuer or aid giver. Device 110 has two supplemental lines. Line 114 is for the rescuer or aid giver to receive air or oxygen from a remote source, the atmosphere or a tank. Inhaling by the rescuer or aid giver is through the assistance of a regulator 116 which allows air from the remote source to be inhaled by the first person. An output device 118 receives the exhaled air from the rescuer or aid giver. Normally the regulator 116 would exhaust such air to the atmosphere. In the present situation, tube 118 is coupled to end 90 of tube 88 for being directed to the victim or patient through housing 12 and device 10.

An alternate embodiment of the invention is shown in FIGS. 6 and 7. Such alternate embodiment is particularly adapted for use when the victim is in the water. In such embodiment, oval-shaped aperture(s) 34 of the embodiment as seen in FIGS. 3, 4 and 5 are replaced by a plurality of essentially circular apertures 122. In order to preclude water fi-from entering the housing, a rigid and preferably cone-shaped member 124 is secured at one end to the housing adjacent to the apertures and formed integrally therewith. Cooperatively associated with preferably cone-shaped member 124 is an elastomeric washer or ring valve member 126. Washer or valve member 126 has its interior edge coupled with respect to the housing, and its exterior periphery normally in contact with the free edge of preferably cone-shaped member 124. Washer or valve member 126 has sufficient memory that apertures 122 are protected from water entering the housing. However, washer or valve member 126 is sufficiently flexible that during the exhaling or air by the second person, the force of the air is sufficient to move washer or valve member 126 from the orientation shown in FIG. 6 to that shown is FIG. 7 to allow the flow of exhaled air from the second person to exhaust from the device. In this manner, the device may be used in and under water without entry of water into the air passageways.

Based on the foregoing, it should be appreciated that the device of the present invention is inexpensive ill construction since most of the parts may be formed out of molded plastic. Thus this device may be produced in a very economical manner and packaged as individual sterized units in packages that may be opened by the emergency care administrator at an onsight location for use in assisting breathing of a victim or patient. After use, due to the inexpensive nature of this product, the device may be discarded so that there is no risk of contaimination through multiple uses.

With respect to the written description of the device of the present insertion, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in tile drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. An assisted breathing interface device comprising:
   a tubular housing with a central longitudinal axis, the tubular housing having an air-entry end and an air-discharge end with a generally cylindrical side wall therebetween, the side wall having an axial bore, a central extent of the bore being formed to constitute a slideway of a predetermined length and at least one radial aperture extending through the side wall in the slideway proximate to the air discharge end;
   a tubular slide valve with a central longitudinal axis co-incident with the axis of the housing, the slide valve having an air-entry end adjacent to the air-entry end of the housing and an air-discharge end adjacent to the air-discharge end of the housing and with a generally cylindrical side wall therebetween, the side wall having a circular cross-sectional configuration externally to slidingly fit within the slideway and having an axial length less than said predetermined length of the slideway whereby when in a first orientation an air path is established from the air-passage end of the housing through the aperture(s) in the side wall of the housing and whereby when in a second orientation the side wall of the slide valve seals the aperture(s) in the side wall from the passage of air therethrough, the slide valve also including at least one axial passageway through the slide valve; and
   a valve member adapted to mate with the slide valve at its air discharge end, wherein the valve member is adapted to assume a first or closed configuration when the slide valve is in the first orientation whereby air from the air discharge end of the housing will cause the slide valve to move to the first orientation, closing the axial air passageway(s) in the slide valve and effecting the flow of air through the aperture(s) in the side wall, and a second or open configuration whereby when the slide valve is in the second orientation, air from the air entry end of the housing will cause the slide valve to close the aperture(s) in the side wall and open the axial passageway(s) in the slide valve to allow the flow of air from the air entry end of the housing to the air discharge end of the housing.

2. The device of claim 1 wherein the valve member adapted to mate with the slide valve is a tension loaded flapper valve or a spring loaded poppet valve.

3. The device of claim 1 and further including a first adapter coupled to the air-entry end of the housing for being coupled to the mouth of a first person for exhaling air through the housing and through the valve member into a second person.

4. The device of claim 1 and further including a second air adapter coupled to the air-discharge end of the housing for being coupled to the mouth of a second person for inhaling air from the first person and for exhaling air through the apertures.

5. The device of claim 4 and further including a washer or supplemental valve positioned to preclude the flow of water into the housing through the aperture(s), but yet allowing the flow of air through the aperture(s) when the device is in use and the second person is exhaling.

6. The device of claim 1 and further including a flexible hose coupled to the air entry end of the housing for administering mouth-to-mouth resuscitation from a remote location.

7. An assisted breathing interface device comprising, in combination:
   a tubular housing with a central longitudinal axis, the tubular housing having an air-entry end and an air-discharge end with a generally cylindrical side wall therebetween, the side wall having a circular cross-sectional configuration along the majority of its axial extent exteriorly, the side wall also having an axial bore with circular cross-sections of varying diameters internally, a central extent of the bore being formed of an increased cross-sectional diameter to constitute a slideway of a predetermined length and with radial apertures extending through the side walls in the slideway proximate to the air discharge end;
   a tubular slide valve with a central longitudinal axis co-incident with the axis of the housing, the slide valve having an air-entry end adjacent to the air-entry end of the housing and an air-discharge end adjacent to the air-discharge end of the housing and with a generally cylindrical side wall therebetween, the side wall having a circular cross-sectional configuration externally to slidingly fit within the slideway and having an axial length less than said predetermined length of the slideway whereby when in a first orientation an air path is established from the air-passage end of the housing through the apertures in the side wall of the housing and whereby when in a second orientation the side wall of the slide valve seals the apertures in the side wall from the passage of air therethrough, the slide valve also including at least one axial air passageway through the slide valve;

a valve member adapted to mate with the slide valve at its air discharge end, wherein the valve member is adapted to assume a first or closed configuration when the slide valve is in the first orientation whereby air from the discharge end of the housing will cause the slide valve to move to the first orientation, closing the axial air passageway in the slide valve and effecting the flow of air through the apertures in the side wall, and a second or open configuration whereby when the slide valve is in the second orientation, air from the air entry end of the housing will cause the slide valve to close the apertures in the side wall and open the axial passageway in the slide valve to allow the flow of air from the air entry end of the housing to the air discharge end of the housing;

a first adapter coupled to the air-entry end of the housing for being coupled to the mouth of a rescuer for exhaling air through the housing and the valve into the victim or patient; and a second air adapter coupled to the air-discharge end of the housing for being coupled to the mouth of a victim or patient for inhaling air from the rescuer and for exhaling air through the apertures.

8. The device of claim 7 wherein the valve member adapted to mate with the slide valve is a tension loaded flapper valve or a spring loaded poppet valve.

9. The device of claim 7 and further including a flexible hose coupled to the air entry end of the housing for administering mouth-to-mouth resuscitation from a remote location.

10. The device of claim 7 and further including a washer or supplemental valve positioned to preclude the flow of water into the housing through the apertures, but yet allowing the flow of air through the apertures when the device is in use and the patient or victim is exhaling.

11. An assisted breathing interface device comprising:

a housing with a central longitudinal axis, the housing having an air-entry end and an air-discharge end with a side wall therebetween, the side wall having an axial bore, a central extent of the bore being formed to constitute a slideway of a predetermined length and with radial apertures extending through the side wall in the slideway proximate to the air discharge end;

a tubular slide valve with a central longitudinal axis co-incident with the axis of the housing, the slide valve having an air-entry end adjacent to the air-entry end of the housing and an air-discharge end adjacent to the air-discharge end of the housing and with a side wall therebetween, the side wall having a cross-sectional configuration externally to slidingly fit within the slideway and having an axial length less than said predetermined length of the slideway whereby when in a first orientation an air path is established from the air-discharge end of the housing through the apertures and whereby when in a second orientation the side wall of the slide valve seals the apertures from the passage of air therethrough, the slide valve also including an axial passageway through the slide valve;

a flapper valve fabricated of a flexible material with memory and normally biassed into a first configuration, the flapper valve coupled with said slide valve, the flapper valve having a radially exterior periphery to mate with the slide valve at its air-discharge end to seal off the flow of air through said axial passageway in said first configuration, whereby air from the discharge end of the housing will close the flapper valve and effect the flow of air through the apertures, the flapper adapted to assume a second configuration curved away from the slide valve whereby when the slide valve is in the second orientation, air from the entry end of the housing will close the apertures and open said axial passageways and allow the flow of air from the entry end of the housing to the discharge end of the housing.

12. The device of claim 11 wherein the air input end of the housing is configured to receive a flexible hose.

13. The device of claim 11 wherein the air-input end of the housing is configured to receive a first adapter for being coupled to the mouth of a first person for exhaling air through the housing and through the slide valve into the second person.

14. The device of claim 13 wherein the discharge end of the housing is configured to receive a second air adapter for being coupled to the mouth of a second person for inhaling air from the first person and for exhaling air through the aperture.

15. The device of claim 13 and further including a flexible hose with a first end coupled to the air entry end of the housing and a second end adapted to receive a first adapter.

16. The device of claim 11 and further including a washer or supplemental valve positioned to preclude the flow or water into the housing through the aperture(s), but yet allowing the flow of air through the aperture(s) when the device is in use and the patient or victim is exhaling.

17. An assisted breathing interface device comprising:

a tubular housing with a central longitudinal axis, the tubular housing having an air-entry end and an air-discharge end with a generally cylindrical side wall therebetween, the side wall having an axial bore, a central extent of the bore being formed to constitute a slideway of a predetermined length, a plurality of apertures extending through the side wall in the slideway proximate to the air discharge end, a rigid, generally cone shaped member secured to the housing and a supplemental valve having an interior edge which is cooperatively associated with the cone-shaped member wherein the interior edge of the supplemental valve is coupled to the housing and is in movable contact with the free edge of the cone-shaped member;

a tubular slide valve with a central longitudinal axis co-incident with the axis of the housing, the slide valve having an air-entry end adjacent to the air-entry end of the housing and an air-discharge end adjacent to the air-discharge end of the housing and with a generally cylindrical side wall therebetween, the side wall having a circular cross-sectional configuration along its axial extent externally to slidingly fit within the slideway and having an axial length less than said predetermined length of the slideway whereby when in a first orientation an air path is established from the air-discharge end of the housing through the apertures in the side wall of the housing and whereby when in a second orientation the side wall of the slide valve seals the apertures in the side wall from the passage of air therethrough, the slide valve also including an axial passageway through the slide valve; and a valve member adapted to mate with the slide valve at its air discharge end, wherein the valve member is adapted to assume a first or closed configuration when the slide valve is in the first orientation whereby air from the discharge end of the housing will cause the slide valve to move to the first orientation, close the axial passageway in the slide valve and effect air flow through the apertures in the side wall, and a second or open configuration whereby, air from the air entry end will cause the slide valve to close the apertures in the side wall and open the axial passageway in the slide valve to allow the flow of air from the air entry end of the air discharge end of the housing.

18. The device of claim 17 wherein the valve member adapted to mate with the slide valve is a tension loaded flapper valve or a spring loaded poppet valve.

19. The device of claim 17 and further including a first adapter coupled to the air-entry end of the housing for being coupled to the mouth of a first person for exhaling air through the housing and the slide valve into a second person, and further including a flexible hose coupled to the air entry end of the housing for administering mouth-to-mouth resuscitation from a remote location.

20. The device of claim 19 and further including a second air adapter coupled to the air-discharge end of the housing for being coupled to the mouth of said second person for inhaling air from the first person and for exhaling air through the apertures.

* * * * *

UNITED STATES PATENT AND TRADEMARK OFFICE
CERTIFICATE OF CORRECTION

PATENT NO.   :   5,398,673
DATED        :   March 21, 1995
INVENTOR(S)  :   Barnum B. Lambert It is certified that error appears in the above-indentified patent and that said Letters Patent is hereby corrected as shown below:

Column 1, line 48, "fitlid" should read -- fluid --.
Column 1, line 51, "fitlid" should read -- fluid --.

In Claim 4, Column 8, line 34, "claim 1" should read -- claim 3 --.

Signed and Sealed this

Twenty-first Day of November, 1995

Attest:

BRUCE LEHMAN

Attesting Officer                    Commissioner of Patents and Trademarks